United States Patent
Stauffer

(10) Patent No.: US 7,084,308 B1
(45) Date of Patent: Aug. 1, 2006

(54) MANUFACTURE OF FORMALDEHYDE FROM METHYL BROMIDE

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 0 days.

(21) Appl. No.: 11/192,807

(22) Filed: Jul. 29, 2005

(51) Int. Cl.
*C07C 45/30* (2006.01)

(52) U.S. Cl. .................................... 568/472; 568/490

(58) Field of Classification Search ............... None
See application file for complete search history.

(56) References Cited

U.S. PATENT DOCUMENTS 4,523,040 A * 6/1985 Olah ........................ 568/671
6,822,123 B1   11/2004 Stauffer .................... 568/475

* cited by examiner

*Primary Examiner*—Sikarl A. Witherspoon
(74) *Attorney, Agent, or Firm*—Young & Basile, P.C.

(57) ABSTRACT

A process is provided for the manufacture of formaldehyde from methyl bromide. In the process, methyl bromide is oxidized with air over a catalyst to give formaldehyde and hydrogen bromide. In a preferred embodiment of the invention, a mixture of two different catalysts are employed, one to promote hydrolysis of methyl bromide to methyl alcohol and the other to promote the oxidation of methyl alcohol to formaldehyde.

6 Claims, 1 Drawing Sheet

MANUFACTURE OF FORMALDEHYDE FROM METHYL BROMIDE

FIELD OF THE INVENTION

The present invention relates to a process for producing formaldehyde from methyl bromide. A heterogeneous catalyst is used to oxidize methyl bromide with air to produce formaldehyde and hydrogen bromide. When integrated with the manufacture of methyl bromide from synthesis gas and hydrogen bromide, the present invention offers an attractive route to formaldehyde.

BACKGROUND OF THE INVENTION

In U.S. Pat. No. 6,822,123, a process was disclosed for the production of formaldehyde from methyl chloride. This process makes use of a catalytic reaction to oxidize methyl chloride with air to give formaldehyde and hydrogen chloride. the benefits of this scheme sere enumerated and included freeing the manufacture of formaldehyde from a dependence on methanol as a raw material.

Because merchant methyl bromide is considerably more expensive than methyl chloride, there would appear to be no advantage in substituting methyl bromide for methyl chloride in a process to manufacture formaldehyde. The drawback of using methyl bromide, however, disappears when byproduct hydrogen bromide is recycled to produce more methyl bromide. This result can be achieves by reacting hydrogen bromide with synthesis gas to form additional methyl bromide. Furthermore, in this recovery process, higher yields of methyl bromide can be obtained than achieved in the production of methyl chloride by the chlorination of methane.

Besides this advantage, other objects, features and benefits of the present invention will be recognized from the following description of the process.

SUMMARY OF THE INVENTION

In one particular embodiment of the invention, methyl bromide is oxidized with oxygen from air over a catalyst to give formaldehyde and hydrogen bromide. After separating the hydrogen bromide from the reaction products, formaldehyde is obtained.

The catalyst used in the reaction to convert methyl bromide to formaldehyde may be of two forms. One type of catalyst consists of particles or pellets of uniform composition. The second type of catalyst consists of an intimate mixture of particles or pellets of two distinct compositions.

The reaction is carried out at a temperature in the range of approximately 250° C. to approximately 400° C. The process is operated at essentially atmospheric pressure, but higher pressures up to about 10 bar may be employed. Preferably, the hydrogen bromide byproduct is reacted with a synthesis gas to form the methyl bromide for the principal reaction.

Other applications of the present invention will become apparent to those skilled in the art when the following description of the best mode contemplated for practicing the invention is read in conjunction with the accompanying drawings.

BRIEF DESCRIPTION OF THE DRAWING

The single FIGURE is a diagram of an apparatus for carrying out the invention.

DETAILED DESCRIPTION OF THE PROCESS

Figure 1:
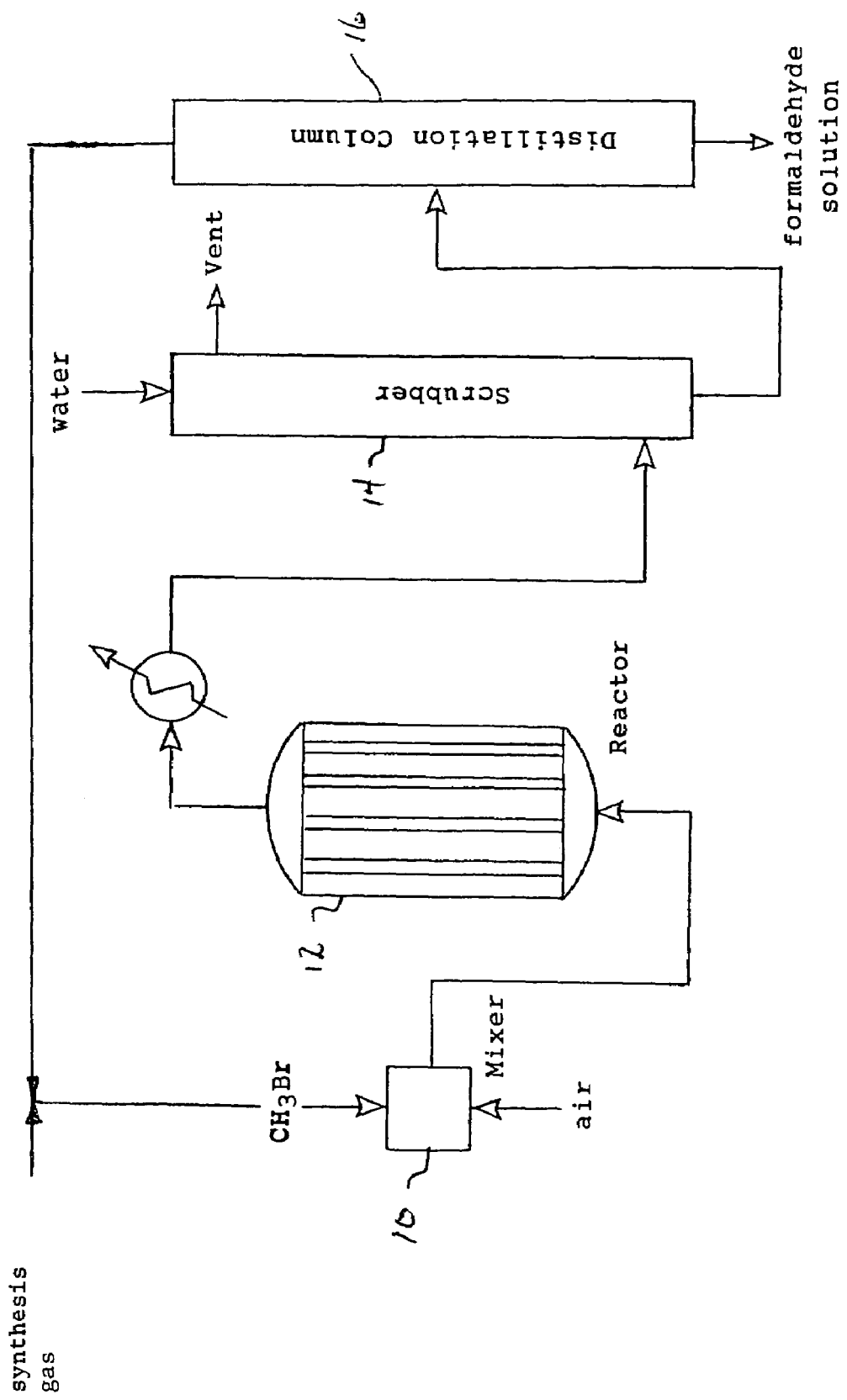

In the process of the present invention, methyl bromide ($CH_3Br$) is oxidized by oxygen ($O_2$) from air in a mixer (10) to produce formaldehyde ($CH_2O$) and hydrogen bromide (HBr). A catalyst is required for this reaction to prevent the complete oxidation of methyl bromide to carbon dioxide. As a result, high yields of formaldehyde are obtained. The conversion of methyl bromide to formaldehyde by the present invention can be given by the following equation:

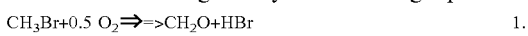

$$CH_3Br + 0.5\ O_2 \Rightarrow\Rightarrow CH_2O + HBr \qquad 1.$$

The reaction that is represented by the above equation essentially goes to completion. From thermodynamic data for Gibbs energies of formation and for enthalpies, equilibrium constants were calculated. At 250° C. log $K_P$ is equal to 15.12 and at 400° C. log $K_P$ equals 12.83. The thermodynamic data also indicate that the reaction is highly exothermic. Under standard conditions, the heat of reaction is 26.17 k cal. per mol.

The success of the process depends primarily on the selection of the catalyst. To understand this requirement, the reaction mechanism is premised to consist of two reaction steps occurring in series. First, methyl bromide is hydrolyzed with water ($H_2O$) to give methyl alcohol ($CH_3OH$) and hydrogen bromide. Second, the methyl alcohol formed in the first step is oxidized with oxygen to form formaldehyde and water. These two steps can be represented by the following equations:

$$CH_3Br + H_2O \Rightarrow\Rightarrow CH_3OH + HBr \qquad 2.$$

$$CH_3OH + 0.5\ O_2 \Rightarrow\Rightarrow CH_2O + H_2O \qquad 3.$$

The above two equations can be combined to give equation 1 above.

The water required for the first reaction step is supplied by the water released in the second reaction step. Some moisture, however, may be required to initiate the reactions. This need can be met, for example, by the humidity of the air used in the process.

Both reactions represented by equations 2 and 3 require catalysts. The first reaction step in which methyl bromide is hydrolyzed to methyl alcohol may be catalyzed by salts of copper, zinc, and bismuth or by alumina gel at a temperature in the range of 280° to 350° C. The hydrolysis of methyl bromide proceeds more easily than the hydrolysis of methyl chloride because the dissociation energy for the bromine-carbon bond in methyl bromide is 284 k joules per mol, which is significantly less than 339 k joules per mol, the disassociation energy for the chlorine-carbon bond in methyl chloride.

The second reaction step whereby methyl alcohol is oxidized to formaldehyde is catalyzed by an iron-molybdenum oxide catalyst, which may be enhanced with chromium oxide. Other catalysts that have been reported to oxidize methyl alcohol include vanadium pentoxide and copper. The oxidation reaction is carried out at a temperature in the range of 250° C. to 400° C.

The above data suggests one approach to catalyst selection. The catalyst could be designed to have a composition that promotes both hydrolysis and oxidation. Such a catalyst might comprise a copper salt that has been shown to be effective for the hydrolysis of methyl bromide as well as for the oxidation of methyl alcohol.

The other approach is to employ two separate catalysts that are commixed. One catalyst, say aluminum gel, would promote hydrolysis and the second catalyst, for example, iron oxide-molybdenum oxide would promote oxidation. Certain catalysts, such as precipitated iron-copper used in Fischer-Tropsch Synthesis are known to be susceptible to poisoning by chlorides. Thus, the avoidance of chlorides in the present invention is considered to be a positive feature.

Because of the exothermic nature of the process, some means needs to be provided to remove the heat of reaction. This object is conveniently accomplished by employment a shell and tube reactor 12. Methyl bromide, which has a boiling point of 3.5° C. and is easily stored as a liquid, is vaporized before being mixed with air and fed to the reactor. The exit gases from the reactor are cooled with water at 14 and then scrubbed in a column 16 to remove the formaldehyde and byproduct hydrogen bromide. With a solubility of 221 gm. per 100 ml. of cold water, hydrogen bromide is readily absorbed. Formaldehyde can be recovered by distillation.

In a commercial application of the invention, the byproduct hydrogen bromide is reacted with a synthesis gas such as 67% CO, 33% $H_2$ to form the methyl bromide used in the principal reaction.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A process for the manufacture of formaldehyde from methyl bromide comprising the steps of:

Reacting methyl bromide with oxygen over a catalyst to give formaldehyde and hydrogen bromide, and separating the formaldehyde from the reaction products.

2. A process according to claim 1 in which the catalyst is comprised of an intimate mixture of particles of two different compositions, one composition which promotes the hydrolysis of methyl bromide to methyl alcohol, and the other composition which promotes the oxidation of methyl alcohol to formaldehyde.

3. A process according to claim 1 in which the reaction is carried out at a temperature in the range of about 250° C. to about 400° C.

4. A process according to claim 1 in which the reaction is carried out at a pressure in the range of 1 atmosphere to 10 atmospheres.

5. A process according to claim 1 in which the reaction is carried out in the presence of water.

6. A process according to claim 1, including the additional step of reacting the hydrogen bromide with synthesis gas to form methyl bromide.

* * * * *